United States Patent [19]

Tovrog et al.

[11] 4,322,562

[45] * Mar. 30, 1982

[54] OXIDATION PROCESS USING METAL NITRO OR NITROSYL COMPLEX

[75] Inventors: Benjamin S. Tovrog, Naperville, Ill.; S. Elliot Diamond, New Providence; Frank Mares, Whippany, both of N.J.

[73] Assignee: Allied Corporation, Morristown, N.J.

[*] Notice: The portion of the term of this patent subsequent to Mar. 4, 1997, has been disclaimed.

[21] Appl. No.: 218,321

[22] Filed: Dec. 19, 1980

Related U.S. Application Data

[63] Continuation-in-part of Ser. No. 86,920, Oct. 22, 1979, abandoned, and a continuation-in-part of Ser. No. 927,194, Jul. 24, 1978, Pat. No. 4,191,696.

[51] Int. Cl.$^3$ .................. C07C 45/35; C07C 45/34
[52] U.S. Cl. ............................. 568/401; 568/400; 568/475; 568/470; 568/431; 568/360; 568/320
[58] Field of Search .............. 568/320, 360, 470, 431, 568/475, 401, 321, 322

[56] References Cited

U.S. PATENT DOCUMENTS

| | | | |
|---|---|---|---|
| 3,404,185 | 10/1968 | Thomas et al. | 568/321 |
| 3,458,547 | 7/1969 | Cofrez et al. | 568/391 |
| 3,927,111 | 6/1976 | Robinson | 568/449 |
| 3,965,185 | 6/1976 | Young | 568/321 |
| 3,981,921 | 9/1976 | Bohnholdt et al. | 568/347 |
| 3,989,801 | 11/1976 | Field et al. | 424/385 |
| 4,026,947 | 5/1977 | Costantini et al. | 260/344 |
| 4,046,813 | 9/1977 | Brenner | 568/344 |
| 4,100,208 | 7/1978 | Maspero et al. | 568/322 |
| 4,104,312 | 8/1978 | Angstadt et al. | 568/342 |

OTHER PUBLICATIONS

Keene et al., J.A.C.S., vol. 99, p. 14 (1977).
Clarkson et al., Inorg. Chem., vol. 12, pp. 1527–1534 (1973).

*Primary Examiner*—Natalie Trousof
*Assistant Examiner*—James H. Reamer
*Attorney, Agent, or Firm*—A. M. Doernberg; R. A. Harman; G. H. Fuchs

[57] ABSTRACT

An oxidation process in which a metal nitro complex transfers an oxygen atom from the nitro ligand to a substrate; especially such process conducted cyclically or catalytically using molecular oxygen as the oxygen source. Metal nitrosyl complex is formed as a coproduct together with an oxidation product of the substrate. In a cyclic process, nitrosyl ligand of the metal nitrosyl coproduct is reoxidized by molecular oxygen in presence of a monodentate base such as pyridine to nitro ligand; and the nitro complex, thus regenerated, can be used again to oxidize the substrate. In a catalytic process, using an activator such as a Lewis acid with alcohols or divalent palladium with olefins, elemental oxygen maintains a concentration of nitro ligand in the reaction mixture. In particular the metal is a Group VIII metal, especially cobalt and the ligand is saloph or tetraphenylporphyrin.

15 Claims, No Drawings

OXIDATION PROCESS USING METAL NITRO OR NITROSYL COMPLEX

This application is a continuation-in-part of our co-pending application Ser. No. 086,920 filed Oct. 22, 1979 now abandoned and of our prior application Ser. No. 927,194 filed July 24, 1978 now U.S. Pat. No. 4,191,696; and incorporates by reference the entire disclosure of each of said prior applications except to the extent, if any, that the same may be inconsistent herewith.

BACKGROUND OF THE INVENTION

This invention relates to a new oxidation process, using metal nitro or nitrosyl complexes to transfer oxygen to a substrate. Especially the invention relates to oxidation using cobalt as the metal and molecular oxygen as the oxygen source.

Cobalt nitro complexes obtained by air oxidation of the nitrosyl complexes in presence of a nitrogen or phosphorus base are known (Inorganic Chemistry, volume 12 of 1973, pages 1528–1534); but no process has heretofore been proposed, so far as we are aware, wherein such complexes function to bring about the oxidation of a substrate.

In the prior art certain oxidation processes using molecular oxygen as the oxygen source are known. In general such processes operate by adsorption on metal oxide catalyst from vapor phase; or proceed in vapor phase or liquid phase by a pathway involving peroxide and free radicals. Such reactions may not be selective for oxidation of particular structures to particular products and/or may not be broadly applicable to a given chemical class of compounds.

Prior to the filing of this application, chemically catalyzed electrochemical oxidation has been disclosed in presence of ruthenium nitro complex and aqueous base, whereby the net effect is to neutralize the base and oxidize a substrate. (J.A.C.S. 99:14/July 6, 1977—Keene et al.)

Also disclosed is production of metal nitrito compounds wherein at least one nitrito group is covalently bonded through the oxygen atom to at least one metal atom. Such compounds, e.g., those with iron or copper, are shown to catalyze oxidation of molecules such as methane or propane to the corresponding primary alcohol, and propylene to propylene oxide (U.S. Pat. No. 3,989,801 of Nov. 2, 1976 to B. O. Field et al.).

SUMMARY OF THE INVENTION

In the present process, any one of a variety of oxidizable structures can be selectively oxidized to a specific oxidation product as the principal product. Conditions of temperature, pressure and solvent can be varied to provide convenient reaction rates and conditions. In particular, ethylene can be thus oxidized to acetaldehyde, propylene can be oxidized to acetone, and higher olefins can be oxidized to ketones; and in presence of organic acid solvent, olefins can be oxidized to alkenyl esters.

We have found that metal nitro complexes are effective oxygen carriers. Accordingly when an oxidizable substrate is provided, and such metal nitro complex of a transition metal is provided in the oxidation reaction mixture, the nitro ligand of said complex can oxidize the substrate and thus be reduced to a nitrosyl ligand. After such reduction to nitrosyl ligand, the nitrosyl complex can be isolated and reoxidized to nitro complex by use of molecular oxygen in presence of an added base, thereby enabling a cyclic process of oxidation with molecular oxyge as the oxygen source to be carried out.

In the presence of an activator as set out hereinafter, the nitrosyl ligand can be oxidized by elemental oxygen maintained in continuous contact with the reaction mixture, whereby the metal nitro or nitrosyl complex functions as a catalyst for the oxidation of the substrate by elemental oxygen. Such activation, we have found, is obtained for the oxidation of alcohols by forming a complex between the nitro or nitrosyl ligand of the metal complex, and a Lewis acid, to activate the oxidation of olefins by the subject metal nitro or nitrosyl complexes, a complex of an olefin with a divalent palladium compound, such as the known (ethylene) palladium chloride dimer, is effective.

We have found that the nitrosyl complexes are more active catalysts than the nitro complexes; probably because the base such as pyridine, included in the nitro complexes, is released at least in part, and reacts with the activator, whether it is a Lewis acid or a divalent palladium compound.

DRAWINGS

This invention is not susceptible of illustration by a drawing.

DETAILED DESCRIPTION

To describe now more particularly the details of our invention, the transition metal which forms the central atom of the metal nitro complex oxidizer is more especially a Group VIII metal such as in particular, cobalt, rhodium, ruthenium, nickel. The metal nitro complexes used as catalysts in accordance with this invention can be represented by the general formula $BM(L_4)NO_2$ and the metal nitrosyl complexes can be represented by $M(L_4)NO$; "M" being a transition metal, "$L_4$" being any number or any combination of monodentate, bidentate, tridentate and tetradentate ligands such as to provide four bonding sites, "B" being a monodentate base ligand, "$NO_2$" being the nitro ligand i.e. $-N(=O)O$, and NO being the nitrosyl ligand. The nitro and nitrosyl ligands are each bound to the metal atom of the complex via the nitrogen atom.

Particularly useful is the complex where M is $Co^{+3}$, $L_4$ is tetraphenylporphyrin ligand, or saloph ligand of formula $[1,2\text{-}(ortho\text{-}OC_6H_4CH=N)_2C_6H_4]^2$ and B (if present) is pyridine. Other complexes which are useful in our process are cobalt complexes with ligands containing oxygen, nitrogen and/or sulfur donor atoms. The ligand can be tetradentate, for example saloph, salen i.e. $[1,2\text{-}(ortho\text{-}OC_6H_4CH=N)_2C_6H_4]^{2-}$, N,N'-ethylenebis (monothioacetylacetoniminate)$^{2-}$, phthalocyanin$^{2-}$ and tetraphenylporphyrin$^{2-}$. Also the ligand can be bisbidentate, for example bis(dimethyldithiocarbamate)$^-$, bis(dimethylglyoximate)$^-$, bis(dicyano 1,2-dithiolene)$^-$, bis(ethylenediamine) and bis(acetylacetonate)$^-$. The ligands can also be tetrakis monodentate ligands such as ammonia. Such complexes can be prepared by the same or similar procedures as used in the prior art, such as the above-cited Inorganic Chemistry article.

The quantity of such complex used is not critical and can be as much as equimolar with the compound to be oxidized, or can be down to a small fraction of that quantity.

In the oxidation of alcohols, activators which can be used include complexes of $Li^+$, $Mo^{6+}$, $W^{6+}$, $V^{5+}$, $Sn^{4+}$, $Al^{3+}$, $B^{3+}$, $Ga^{3+}$; and more generally an organic complex of a transition metal, or Lewis acid such as a compound of a metallic element with an element of Group VII. When an alcohol is the substrate, it is advantageous to use as activator of cocatalyst a Lewis acid such as boron trifluoride etherate, $LiPF_6$ and $LiBF_4$. (To the extent practical, presence of water should be avoided since water decomposes the metal nitro complex in presence of Lewis acids). The compound molybdenumdioxide(dialkyldithiocarbamate) is representative of organic complexes of transition metals useful as activators. The quantity of activator used is not critical and can be much less or much more, on a molar basis, than the quantity of nitro or nitrosyl complex used.

In addition to primary and secondary alcohols, substrates which we have found amenable to oxidation by our process include compounds having isolated olefinic bonds. When a compound having an isolated olefinic bond is the substrate to be oxidized, a useful activator in accordance with this invention is a divalent palladium compound which forms a complex with said olefinic bond, such as palladium dichloride.

When our process is used to oxidize a primary alcohol the principal product is the aldehyde and from a secondary alcohol, the principal oxidation product is the ketone, having the same skeletal structure as said primary of secondary alcohol. In particular, benzyl alcohol can be oxidized to benzaldehyde and cyclic alcohols such as the cyclopentanols, cyclohexanols, cycloheptanols and cyclooctanols, substituted and unsubstituted, can be oxidized to the corresponding ketones, namely cyclopentanone, cyclohexanone, cycloheptanone and cyclooctanone, respectively.

From compounds having at least one isolated olefinic bond, which compounds can be aliphatic, alicyclic, or alkenylaromatic, activated by formation of a complex with divalent palladium, products which can be obtained are acetaldehyde from ethylene, acetone from propylene and ketones from higher olefins; and alkenyl esters from olefins when an organic acid solvent is used.

The following examples are illustrative of our invention and of the best mode we now contemplate for carrying out the invention, but are not be to be interpreted as limiting.

PROCEDURES

Reagents

Cobalt complexes used as starting materials and $(PhCN)_2PdCl_2$ were prepared and purified by published procedures. Vacuum distillation was found satisfactory for purification of $BF_3 \cdot Et_2O$. Dichloromethane and 1,2-dichloroethane were dried over 4 Å molecular sieve. All alcohols and pyridine were used as received.

Co(Saloph)NO (Complex IIa)

Co(saloph) (Marzilli et al. J.A.C.S. 93 1374 of 1971) (1.0 g) was suspended in 25 mL of degassed $CH_2Cl_2$. Nitric oxide (purified by passage through a dry ice-acetone trap and a tower of KOH pellets) was bubbled through the solution. Within a few minutes the red solution darkened to black with the formation of a black precipitate. After one hour, the reaction solution was flushed with argon; the solid was filtered, washed with ether and dried in vacuo; yield 0.81 g (75%). Anal. Calcd for $CoC_{20}H_{14}N_3O_3$: Co, 14.61; C, 59.56; H, 3.50; N, 10.42. Found: Co, 14.84; C, 59.20; H, 3.66; N, 10.30.

This material exhibited a sharp, strong absorption in the IR assigned to $v_{NO}$ at 1660 $cm^{-1}$.

PyCO(saloph)NO₂ (Complex II)

Oxygen was bubbled through 50 mL of $CH_2Cl_2$ containing 1 g Co(saloph)NO and 2 mL pyridine at room temperature. The reaction was continued until most of the solvent had evaporated (6 hours) and the red solid that formed was filtered, washed with ether and air dried; yield 0.89 g (72%). Anal. Calcd for $CoC_{25}H_{19}N_4O_4$: C, 11.82; C, 60.25; H, 3,84; N, 11.24. Found: Co, 1206; C, 59.86; H, 4.05; N, 11.38. The IR spectrum of the nitro product did not contain a band in the Co—NO region, but exhibited new bands at 1320, 1220 and 820 $cm^{-1}$ which were assigned to Co—$NO_2$ vibrations.

PyCo(TPP)NO₂ (Complex-"TPP" stands for tetraphenylporphyrin)

0.6 g Co(TPP)NO (Complex Ia-Wayland et al., J.A.C.S. 96 2795 of 1974) was dissolved in 30 mL $CH_2Cl_2$ and 1.2 pyridine. Dry oxygen was bubbled vigorously through the solution for four hours and then 100 mL of a 1:1 mixture of petroleum ether: hexane was added. The resulting precipitate (0.6 g) was filtered, washed with hexane and dried in vacuo. This material exhibited no IR band at 1690 $cm^{-1}$, but new bands at 1320, 1220 and 820 $cm^{-1}$ were present. Anal. Calcd for $C_{49}H_{35}N_6O_2Co$: C, 73.84; H, 4.19; N, 10.56. Found: C, 72.61; H, 4.61; N, 10.19.

Oxidation of Co(TPP)NO (Complex Ia) by O₂ in the presence of Lewis acids.

Under argon, first Co(TPP)NO (0.139 g, 0.20 mmol), followed by benzyl alcohol (0.53 mL, 5.1 mmol) and then $BF_3 \cdot Et_2O$ (0.125 mL, 1.02 mmol) were added to deoxygenated 1,2-dichloroethane. Then a slow stream of $O_2$ was passed through the solution at room temperature. After 1 hour, the solvent was evaporated in vacuo and the residue was treated with a 1:1 mixture (20 mL) of dichloromethane and n-heptane under argon. The resulting precipitate was filtered off, washed with four portions of a dichloromethane/n-heptane mixture (20 mL) and dried in vacuum. The IR spectrum of this material shows no Co-NO band. Instead, new bands are observed at 1208, 1313 and 1490 $cm^{-1}$ as well as a broad band at 950–1100 $cm^{-1}$.

Oxidation of alcohols by oxygen catalyzed by cobalt nitro or nitrosyl complexes.

Oxygen-saturated solutions of the substrate (ca. 10 mmol), biphenyl (internal standard, ca. 0.5 mmol) and the cobalt nitro or nitrosyl complex shown in Table I below (ca. 0.4 mmol) in 1,2-dichloroethane (10 mL) were placed into a Fisher-Porter bottle equipped with a poly-TFE coated stirring bar. At this time, the reactor was closed, pressurized with oxygen to the required pressure and immersed into a controlled temperature bath.

Aliquots were removed by a gas-tight syringe at appropriate intervals for gas chromatographic analysis on either a Hewlett-Packard 5830A equipped with a flamge ionization detector or on a Hewlett-Packard 5710A and/or Perkin-Elmer 3920B instrument equipped with thermal conductivity detectors. Analyses of cycloheptanol oxidation products were performed with a 1.83 m (6 ft) column containing 10% Carbowax supported on 80/100 Supelcoport. The benzyl alcohol oxidations were analyzed on a 1.22 m (4 ft) column packed with 5% Silar 5CP supported on 80/100

Gas-Chrom Q. Prior to injection into the column, BF$_3$.Et$_2$O was removed to avoid decomposition of column materials. This is accomplished by addition of one drop of pyridine and ca. 2 mL of hexane to 0.5 mL of reaction solution aliquots. Filtration of the mixture removed the BF$_3$.pyridine complex prior to injection on the gas chromatograph ("gc").

Concentrations of the solution components were determined by computer integrations employing biphenyl as the internal standard. Isolation of complexes from the reaction mixture was accomplished by removing solvent in vacuo from reaction aliquots. The resulting oil was triturated with petroleum ether, giving a solid which was filtered and air dried.

Illustrative runs are summarized in Table I below. Table I includes as comparisons, Run 1 (no Lewis acid) and Runs 6 and 7 (using Co(TPP) as such or as the iodide, without a nitro or nitrosyl ligand). Comparing Run 2 vs. Run 5 of Table I indicates that the nitrosyl complex (Ia), Co(TPP)NO, is a more active catalyst than the nitro complex (I), PyCo(TPP)NO$_2$.

Procedure for oxidation of olefin by oxygen catalyzed by cobalt nitro or nitrosyl complexes.

Olefin was passed through an approximately 0.02 M solution of (PhCN)$_2$PdCl$_2$ (Kharash et al., J.A.C.S. 60 882 of 1938) in the appropriate solvent at 25° C. When the olefin complex had formed, cobalt nitro (I or II) or cobalt nitrosyl (Ia or IIa) complexes were added (ca. stoichiometric i.e. ca. 0.01 M). Then the desired gas mixture at a flow of ca. 24 mL of olefin/min. and ca. 4 mL of O$_2$/min. was passed through the solution. The products were collected in a cooling trap. The cooling trap consisted of a solvent (THF for acetaldehyde and acetone, and toluene for vinyl acetate collection) and a known amount of biphenyl (gc internal standard). The temperature of the trap was maintained at either $-77°$ C. (for collection of acetaldehyde and acetone) or $-10°$ C. (for vinyl acetate collection). The reaction flask was immersed into a controlled temperature oil bath. At the appropriate time intervals, samples were removed from the traps and analyzed on a HewlettPackard 5830A gas chromatograph equipped with a flame ionization detector with either a 2.44 m (8 ft) Porapak QS column or with a 1.8 m (6 ft) column containing 10% Carbowax supported on 80/100 Supelcoport.

The runs of Table II illustrate catalytic oxidation of olefins in accordance with this invention. In Table II, Runs 1–5 and 9, bis(benzonitrile)palladium dichloride (IV) was used as the divalent palladium compound activator. In Runs 6 and 7 of Table II using acetic acid solvent, palladium(II) acetate was used as the activator; and vinyl acetate was formed catalytically as the product. In comparison Run 8, using palladium acetate but no metal nitro or nitrosyl complex, the oxidation was not catalytic and palladium metal precipitated. In Table II, the relatively inferior result in Run 2 is attributed to the low partial pressure of ethylene in the feed gas.

Comparison of Run 4 vs. Run 5 of Table II indicates that the Co(TPP)NO complex is a more active catalyst than the PyCo(TPP)NO$_2$ complex.

Two examples of stoichiometric oxidation of olefins using Complex II as oxidizing agent are given, illustrating the relation between such stoichiometric oxidation and catalytic oxidation as illustrated in Table II.

EXAMPLE 1 (Stoichiometric Oxidation)

Bis(benzonitrile)palladium dichloride (0.1378 g) was dissolved in 210 mL of dry degassed 1,2-dichloroethane under a flow of oxygen-free gas (argon). Ethylene was bubbled in and the yellow color of (ethylene)palladium chloride dimer formed rapidly. Cobalt(saloph)-(pyridine) nitro complex (Complex II) (0.1045 g) was added; and the vessel, stoppered to maintain the solution under 1 atm. of ethylene pressure, was immersed in a 45° C. oil bath. Gas chromatography (on Porapak QS column) of aliquots from the reaction solution showed formation of acetaldehyde, reaching after about 90 minutes a value of 86.1% based on the cobalt complex initially added.

Infrared spectra of a solid product isolated from the reaction mixture showed that the Co—NO$_2$ group had been reduced to Co—NO, indicating that the oxygen present in the acetaldehyde product originated from the Co—NO$_2$ group. That the only role of Pd$^{2+}$ was as an activator, and such Pd$^{2+}$ was not itself reduced during the acetaldehyde production, was verified by adding acetic acid (1 mL) to the reaction mixture. An atmosphere of ethylene at 1 atmosphere pressure was again introduced over the solution, and the vessel was then stoppered and immersed in a 45° C. oil bath. Thereupon vinyl acetate, the expected product from oxidation of ethylene by Pd$^{2+}$ in acetic acid, was formed to the extent of 93% based on Pd present.

The above noted Co—NO coproduct, present in solids isolated from the reaction mixture, can be reoxidized to the starting cobalt nitro complex by molecular oxygen in presence of base. For example, the solid materials is dissolved in dichloromethane and the solution is filtered. Pyridine is added to the filtrate and oxygen is bubbled into the stirred solution. Formation of the orange-red color of the cobalt nitro complex (Complex II) is observed. When the reoxidation is judged to be at an end the resulting Co—NO$_2$ complex can be isolated.

EXAMPLE 2 (Stoichiometric Oxidation)

This example was carried out essentially as for Example 1, using 0.1437 g of bis(benzonitrile)palladium dichloride dissolved in 15 mL of dry degassed 1,2-dichloroethane under argon, into which propylene was bubbled. The initially orange solution turned yellow. After about 30 minutes, cobalt(saloph) (pyridine) nitro complex (Complex II) (0.1224 g) was added under a propylene atmosphere. GC analysis (on Porapak QS column), after about one hour, showed that the product was propionaldehyde and/or acetone (not propylene oxide).

The volatiles were stripped out by bubbling argon through the solution heated in a 45° C. oil bath, and were condensed in an acetone/solid carbon dioxide trap.

The resulting product was analyzed by GC (on 10% Carbowax column) to discriminate between propionaldehyde and acetone, showing the product to be acetone.

Upon pumping off the atmosphere over the residue to dryness and taking up the solids in petroleum ether, the residue was found by infrared analysis to contain the Co—NO group, and also a substantial proportion of the Co—NO$_2$ group.

The production of acetone in the above Example is estimated at about 25 mole percent yield based on the cobalt nitro complex initially added.

The Co—NO coproduct can be reoxidized to regenerate the Co—NO$_2$ complex (Complex II) by molecular oxygen in presence of a base, as in the above Example 1.

Catalytic Oxidation Runs

Catalytic oxidations using the above described procedures, including presence of an activator and presence of oxygen in contact with the reaction mixture, are outlined in Tables I and II below.

TABLE I

Oxidation of Alcohols Catalyzed by a Combination of Cobalt Nitro or Nitrosyl Complex with Lewis Acid[a]

| Run # | Complex | Lewis Acid/Co (Ratio) | Time (min) | Moles of Product:[b] Moles of Co |
|---|---|---|---|---|
| | Benzyl Alcohol | | | |
| 1 | PyCo(TPP)NO$_2$ (I) | none | 240 | 0 |
| 2 | I | BF$_3$ . Et$_2$O (5.0) | 60 | 7.9 |
| | | | 240 | 11.9 |
| 3 | I | LiPF$_6$ (5.0) | 60 | 6.2 |
| | | | 240 | 7.9 |
| 4 | Co(TPP)NO (Ia) | none | 240 | 0 |
| 5 | Ia | BF$_3$ . Et$_2$O (5.0) | 60 | 10.1 |
| | | | 240 | 14.3 |
| 6 | Co(TPP) | Bf$_3$ . Et$_2$O (5.0) | 60 | 0.2 |
| 7 | Co(TPP)I | BF$_3$ . Et$_2$O (5.0) | 60 | 0.8 |
| | Cycloheptanol | | | |
| 8 | I | BF$_3$ . Et$_2$O (5.0) | 90 | 1.5c |
| 9 | I | BF$_3$ . Et$_2$O (5.0) | 60 | 4.2 |
| 10 | II | BF$_3$ . Et$_2$O (5.0) | 90 | 1.5c |
| | Mixture of Cyclopentanol:Cycloheptanol = 1:1 | | | |
| 11 | I | BF$_3$ . Et$_2$O (95.0) | 270 | 3.5d |

[a]Unless stated otherwise, the oxidation was run at 60° C. under 344.7 kPa (50 psig) of O$_2$.
[b]The product is either benzaldehyde or cycloheptanone.
[c]At 103.4 kPa (15 psig) of O$_2$.
[d]Only cycloheptanone was found in the reaction mixture.

TABLE II

Olefin Oxidation by Molecular Oxygen[a] Catalyzed by Cobalt Complexes

| Run # | Complex | Pd/Co | Solvent | (min) | Moles of Product: Moles of Co |
|---|---|---|---|---|---|
| | Ethylene | | | | Acetaldehyde |
| 1 | II | 1.42 | Diglyme | 240 | 3.2 |
| 2 | II | 2.10 | THF | 360 | 1.0[b] |
| 3 | II | 2.32 | DMF | 120 | 4.1 |
| | | | | 240 | 8.4 |
| 4 | I | 3.09 | Diglyme | 120 | 2.3 |
| | | | | 240 | 4.8 |
| | | | | 360 | 6.8 |
| 5 | Ia | 2.40 | Diglyme | 120 | 6.0 |
| | | | | 240 | 12.2 |
| | | | | | Vinyl Acetate[c] |
| 6 | II | 3.61 | AcOH | 240 | 5.4 |
| 7 | I | 3.47 | AcOH | 120 | 3.6 |
| | | | | 240 | 7.4 |
| | | | | 480 | 12.8 |
| 8 | Pd(OAc)$_2$ | — | AcOH | 420 | 0.89[d] |
| | Propylene | | | | Acetone[e] |
| 9 | I | 2.56 | Diglyme | 480 | 1.7 |

[a]The oxidations were run at 70° C., 1 atm pressure with gas bubbled through a 10 mM solution of I or II in dried solvent using IV as activator unless stated otherwise. The gas flow was 24 mL/min of olefin and 4 mL/min of O$_2$ unless stated otherwise. The products were trapped from the exit gases in THF at 77° C. (acetaldehyde and acetone) or in toluene at −10° C. (vinyl acetate).
[b]The gas flows were 3 mL/min of ethylene, 15 mL/min of O$_2$ and 10 mL/min of Ar.
[c]IV was replaced by Pd(OAc)$_2$ in all oxidations carried out in acetic acid.
[d]Only Pd(OAc)$_2$ (10 mM solution) and no nitro cobalt complex were present in the reaction mixture. The yield is based on Pd(OAC)$_2$. Palladium metal was formed.
[e]The gas flows were 18 mL/min of propylene and 16 mL/min of O$_2$.

We claim:

1. In a process of oxidizing a compound having at least one isolated olefinic bond, in liquid phase using molecular oxygen as the oxygen source, the improvement which comprises in the oxidation reaction mixture a transition metal nitro or nitrosyl complex representable by the general formula BM(L$_4$)NO$_2$ or M(L$_4$)NO respectively, wherein M is a transition metal and L$_4$ is any number or any combination of monodentate, bidentate, tridentate and tetradentate ligands such as to provide four binding sites, B being a monodentate base ligand; NO$_2$ being the nitro ligand—N(=O)O and NO being the nitrosyl ligand each bound to the metal atom via the nitrogen atom; under conditions, including use as activator of a divalent palladium compound which forms a complex with said olefinic bond, whereby the nitro ligand of said metal nitro complex oxidizes said compound and is reduced to a nitrosyl ligand and such nitrosyl ligand is reoxidized by molecular oxygen to nitro ligand.

2. Process of claim 1 wherein elemental oxygen is maintained in continuous contact with the reaction mixture, and the transition metal is a Group VIII metal.

3. Process of claim 2 wherein the activator is bis(benzonitrile)palladium dichloride.

4. Process of claim 3 wherein the compound oxidized is ethylene and the complex is a metal nitrosyl complex of formula M(L$_4$)NO.

5. Process of claim 4 wherein M is Co$^{3+}$ and L$_4$ is saloph ligand formula [1,2-(ortho-OC$_6$H$_4$CH=N)$_2$C$_6$H$_4$]$^{2-}$.

6. Process of claim 4 wherein M is Co$^{3+}$ and L$_4$ is tetraphenylporphyrin ligand.

7. Process of claim 3 wherein the compound oxidized is propylene.

8. Process of claim 7 wherein the complex is a nitrosyl complex, M is Co$^{3+}$ and L$_4$ is tetraphenylporphyrin ligand.

9. Process of claim 7 wherein the complex is a nitrosyl complex, M is Co$^{3+}$ and L$_4$ is saloph.

10. Process of claim 2 wherein said complex is a metal nitro complex of formula BM(L$_4$)NO$_2$.

11. Process of claim 10 wherein said metal is Co$^{3+}$ and B is pyridine.

12. Process of claim 11 wherein L$_4$ is the saloph ligand.

13. Process of claim 12 wherein the compound oxidized is ethylene or propylene.

14. Process of claim 11 wherein L$_4$ is the tetraphenylporphyrin ligand.

15. Process of claim 14 wherein the compound oxidized is ethylene or propylene.

* * * * *

UNITED STATES PATENT AND TRADEMARK OFFICE
CERTIFICATE OF CORRECTION

PATENT NO. : 4,322,562

DATED : March 30, 1982

INVENTOR(S) : Benjamin S. Tovrog, S. Elliot Diamond and Frank Mares

It is certified that error appears in the above-identified patent and that said Letters Patent are hereby corrected as shown below:

Col. 2, line 3 "oxyge" should read --oxygen--;

Col. 3, line 5 "of" should read --or--;

Col. 4, line 4 "PyCO" should read --PyCo--;

line 11 "3,84" should read --3.84--;

line 16 insert --I-- after "Complex";

line 20 insert --mL-- after "1.2";

Col. 5, line 9 delete "s" in "integrations";

Col. 7, line 56 "240" should be in the "(min)" column;

"8.4" should be in the "Acetaldehyde" column;

Col. 8, line 11 "77°C." should read -- -77°C. --;

Col. 8, line 21 (Claim 1, line 4) insert --providing-- after "comprises";

UNITED STATES PATENT AND TRADEMARK OFFICE
CERTIFICATE OF CORRECTION

PATENT NO. : 4,322,562

DATED : March 30, 1982

INVENTOR(S) : Benjamin S. Tovrog et al.

It is certified that error appears in the above—identified patent and that said Letters Patent is hereby corrected as shown below:

Column 8, line 45 (Claim 5, line 2) insert -- of -- after "ligand".

Signed and Sealed this

Eighth Day of June 1982

[SEAL]

Attest:

GERALD J. MOSSINGHOFF

Attesting Officer

Commissioner of Patents and Trademarks